United States Patent [19]
Vis

[11] 4,348,589
[45] Sep. 7, 1982

[54] MICROPHONIC NOISE COMPENSATION FOR AN IONIZATION DETECTOR

[75] Inventor: Petrus N. J. Vis, Eindhoven, Netherlands

[73] Assignee: U.S. Philips Corporation, New York, N.Y.

[21] Appl. No.: 160,702

[22] Filed: Jun. 18, 1980

[30] Foreign Application Priority Data

Jun. 25, 1979 [NL] Netherlands ............................ 7904923

[51] Int. Cl.³ ................................................ H01J 39/28
[52] U.S. Cl. ..................................... 250/387; 250/385; 378/19
[58] Field of Search ................... 250/385, 44 ST, 386, 250/387, 374; 324/118; 307/520, 521; 328/167, 165, 162

[56] References Cited

U.S. PATENT DOCUMENTS

| | | | |
|---|---|---|---|
| 3,339,071 | 8/1967 | Fowler et al. | 250/387 |
| 3,400,268 | 9/1968 | Amano | 250/387 |
| 3,424,981 | 1/1969 | Erdman | 324/118 |
| 3,670,833 | 6/1972 | Tomohiko et al. | 328/165 |
| 3,683,189 | 8/1972 | Garrett | 250/374 |
| 3,991,312 | 11/1976 | Whetten et al. | 250/385 |
| 4,048,503 | 9/1977 | Taylor | 250/385 |

Primary Examiner—Davis L. Willis
Assistant Examiner—Carolyn E. Fields
Attorney, Agent, or Firm—Marc D. Schechter

[57] ABSTRACT

A device for measuring local X-ray absorption differences in a patient or other object has an array of ionization detector elements. Each detector element has a high voltage electrode. The high voltage source for each such electrode has associated with it an alternating voltage source in order to compensate for microphonic interference. The measuring circuit includes a demodulation compensation circuit for separation of the microphonic signal and for removing this interference from the measuring signal.

3 Claims, 2 Drawing Figures

MICROPHONIC NOISE COMPENSATION FOR AN IONIZATION DETECTOR

BACKGROUND OF THE INVENTION

The invention relates to a device for measuring local absorption differences in a cross-section of an object. The device comprises at least one detector which has a gas-filled chamber. In the chamber are arranged, at a comparatively small distance from each other, a high voltage electrode and a signal electrode. A high voltage source is connected to the high voltage electrode and a signal measuring circuit is connected to the signal electrode.

A device of this kind, in the form of an X-ray scanner comprising a series of detectors which can be read separately is known from U.S. Pat. No. 4,048,503. In an apparatus of this kind, movement of the detectors with respect to the object to be examined causes vibrations which result in microphonic interference signals in the detector signal to be measured.

Because of the construction of the detector elements—a high voltage electrode and an adjacent signal electrode which are mounted at a short distance from each other—each measuring chamber constitutes a capacitor whose capacitance is modulated by vibrations of the electrodes. This modulation causes an interference signal in the measuring signal. It has been found that this capacitance modulation is not adequately mitigated even by specially mounting the various electrodes.

SUMMARY OF THE INVENTION

It is an object of the invention to eliminate the noise due to capacitance modulation. To this end, in a device according to the invention the high voltage source includes an alternating voltage source. A demodulation compensation circuit is included in the signal measuring circuit to remove the microphonic interference.

More particularly, according to the invention an alternating voltage signal having a comparatively high frequency is introduced to the detector via the high voltage electrode. This high frequency signal is superposed on the microphonic modulation which has a comparatively low frequency. The microphonic signal can be separated in a device according to the invention, described below. By subtracting the microphonic signal from the direct measuring signal, by using a differentiator circuit, a measuring signal which does not contain the microphonic modulation can be recovered.

In a preferred embodiment, the alternating voltage signal has a frequency of, for example, 1 MHz and an amplitude of, for example, 1 volt. The high voltage applied to the detector is in the hundreds of volts and the measuring frequency is approximately 100 Hz.

Another preferred embodiment includes an X-ray source and a detector system. The detector system is provided with an array of detectors which can separately read incident radiation. The source and the detector system are arranged to be simultaneously rotatable with respect to an object to be simultaneously rotatable with respect to an object to be irradiated.

As a result of the desired fast movements in a device of this kind, comparatively strong vibrations are produced which result in comparatively strong microphonic interference. This interference is removed by means of a circuit according to the invention. The invention may also be used in a device for examining an object which emits an ionizing radiation and which is scanned by means of a detector system in order to determine concentration variations. dr

DESCRIPTION OF THE PREFERRED EMBODIMENTS

Figure 1:
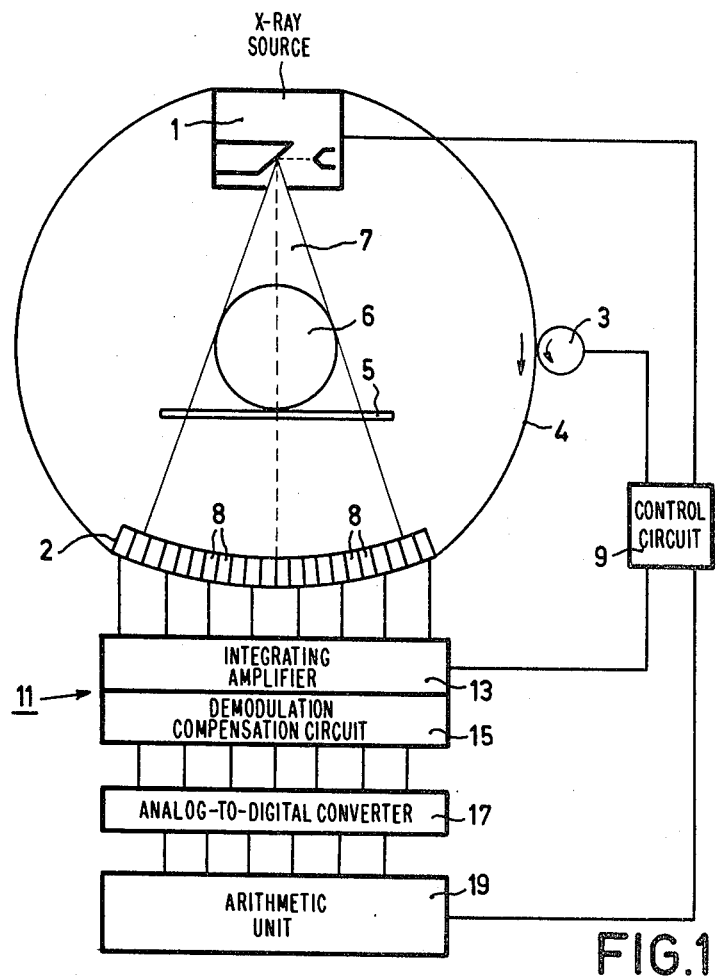
FIG. 1 is a schematic representation of a device for measuring radiation absorption differences, comprising an X-ray source and a detector system.

A device for meaasuring local X-ray absorption differences in a patient for medical diagnostics is shown in FIG. 1. The devices comprises an X-ray source 1 and a detector system 2. Source 1 and detector system 2 are arranged to be rotatable, by means of a rotation device 3 and an annular support 4, around an object 6 situated on a supporting table 5. For devices where the X-ray beam 7 does not fully irradiate the patient, the source 1 and the detector system 2 are also movable, together or separately, toward or away from the patient. Each of the detector elements 8, situated in a shadow of the patient receives X-rays 7 of different amounts of X-ray intensity due to the different absorption by the patient's body parts.

In practical devices, the detector elements 8 are exposed, for example, from 1 to 5 ms, after which the X-ray beam 7 is blanked by means of a control circuit 9 and the detectors are read. The signals are formed during the exposure time, and preferably also for a few ms longer, and are sent to a measuring circuit 11. Circuit 11 comprises an integrating amplifier 13 for amplification and integration over the time period. The integration time and the revolution speed of the source/detector system are coupled via the control circuit 9, so that integration actually takes place over a given measuring angle, in practical cases, for example, over 1°. According to the invention, the measuring circuit 11 also comprises a demodulation compensation circuit 15. As in known devices, the integration signals formed in the measuring circuit 11 are applied to an analog-to-digital converter 17 and subsequently to an arithmetic unit 19 in order to form an absorption image of a slice of the object patient irradiated by the X-ray beam 7.

Figure 2:
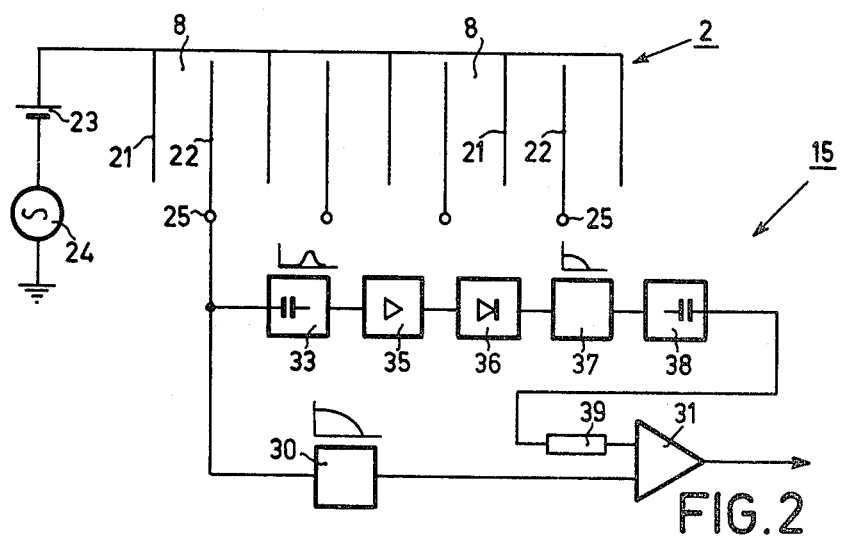
FIG. 2 is a block diagram of a detector system comprising a compensation circuit according to the invention.

FIG. 2 is a block diagram of a preferred embodiment of a demodulation compensation circuit 15. In each of the detector elements 8 of the detector 2, a high voltage electrode 21 and a signal electrode 22 form a capacitor having a capacitance C which may be assumed to be the same for all elements (this is an accurate assumption in the context of the invention). The high voltage electrodes 21 are connected to a high voltage source 23 and an alternating voltage source 24. The signals which are derived from electrodes 25 thus each contain an alternating voltage component. When the detector is in the rest condition so that it is not exposed, each signal contains only this component. The frequency of the alternating voltage is chosen so that it clearly exceeds the highest measuring frequency and so that it can be comparatively simply separated from the signal electronically. It has been found that a frequency on the order of 1 MHz is satisfactory, but any frequency in the range beyond, for example, approximately 10,000 Hz may be used.

If the electrodes of the detector elements start to vibrate, for example, due to the rotation of the detector system around the patient or other object, a low frequency signal component becomes superimposed on the high frequency alternating voltage. It has been found that this low frequency microphonic component is between approximately 100 and 500 Hz in practical devices. When the detector is subsequently exposed, a composite measuring signal is produced which contains the high frequency modulated microphonic component as well as the high frequency modulated real measuring signal which is produced by the charge carriers formed by ionization by the radiation incident on the gas molecules in the measuring chambers. This composite signal is processed, via a filter circuit 30 in which the high frequency alternating voltage component is removed, in a differential amplifier 31. At the same time, the measuring signal is processed in the demodulation compensation circuit 15. The demodulation compensation circuit 15 in this case comprises an isolating filter 33, acting as a bandpass filter or a high-pass filter, an amplifier 35, a diode circuit 36, a low-pass or low bandpass filter 37, a direct current isolating element 38, a control circuit 39 and the differential amplifier 31.

The low frequency real measuring signal is removed from the composite signal in the isolating filter 33. From the signal then recovered, possibly after amplification by amplifier 35, a signal is formed which contains only the microphonic signal component. This microphonic component is separated by a demodulator circuit 36-38 for amplitude modulated signals. Via a control circuit 39 for matching the original amplitude, this signal is applied to the differential amplifier 31 in which it is actually subtracted from the filtered composite signal. As a result, a real measuring signal is produced from which the microphonic component has been removed. The control circuit 39 can be adjusted, for example, on the basis of additional measurement outside the actual examination.

It will be clear that a demodulation compensation circuit must be connected to each detector element 8, and the number of detector elements 8 to be used does not restrict the range of application of the invention. If it is to be expected that different detector elements will supply a microphonic component of substantially the same value and the same phase, a combined demodulation compensation circuit can in principle be used.

A scanning examination device for measuring radiation to be emitted by an object itself, i.e. a device which does not include a radiation source, may comprise two detector devices for measuring in coincidence, both detector devices comprising a demodulation compensation circuit according to the invention.

What is claimed is:

1. A device for measuring local absorption differences in an object, said device comprising a detector comprising:
    a chamber filled with gas;
    a high-voltage electrode in the chamber;
    a signal electrode arranged in the chamber adjacent to, but spaced from, the high-voltage electrode;
    a high-voltage source connected to the high-voltage electrode; and
    a signal measuring circuit connected to the signal electrode;
    wherein, in operation the detector has an output signal at the signal electrode comprising a real measuring signal modulated by a microphonic noise signal;
    CHARACTERIZED IN THAT the device further comprises:
    an alternating voltage source for producing a high-frequency alternating voltage which modulates the high-voltage source and the detector output; and
    a demodulator compensation circuit for isolating the microphonic noise signal from the detector output.

2. A device as claimed in claim 1, CHARACTERIZED IN THAT the demodulation compensation circuit comprises:
    an isolating filter for removing the real measuring signal from the detector output;
    a demodulation circuit for removing the high-frequency alternating voltage from the detector output; and
    a control circuit for matching the remaining detector output to its original amplitude.

3. A device as claimed in claim 1 or 2, CHARACTERIZED IN THAT:
    the high-frequency alternating voltage has a frequency of approximately 1 megahertz and an amplitude of approximately 1 volt;
    the high-voltage source produces a potential difference of some hundreds of volts; and
    the detector is, in operation, rotated around the object at a speed of a few seconds per revolution.

* * * * *